United States Patent
Takahashi et al.

(10) Patent No.: US 11,160,849 B2
(45) Date of Patent: Nov. 2, 2021

(54) NOROVIRUS DEACTIVATOR AND METHOD FOR PRODUCING SAME, METHOD FOR DEACTIVATING NOROVIRUS, METHOD FOR PRODUCING LYSOZYME COMPONENT FOR NOROVIRUS DEACTIVATION USE, PROPHYLACTIC OR THERAPEUTIC AGENT FOR NOROVIRUS INFECTION, AND EXTERNAL PREPARATION FOR SKIN FOR NOROVIRUS DEACTIVATION PURPOSES

(71) Applicants: NATIONAL UNIVERSITY CORPORATION TOKYO UNIVERSITY OF MARINE SCIENCE AND TECHNOLOGY, Tokyo (JP); KEWPIE CORPORATION, Tokyo (JP)

(72) Inventors: Hajime Takahashi, Tokyo (JP); Miki Sato, Fukaya (JP); Takashi Miyashita, Hino (JP); Ryo Sasahara, Fuchu (JP)

(73) Assignees: NATIONAL UNIVERSITY CORPORATION TOKYO UNIVERSITY OF MARINE SCIENCE AND TECHNOLOGY, Tokyo (JP); KEWPIE CORPORATION, Tokyo (JP)

( * ) Notice: Subject to any disclaimer, the term of this patent is extended or adjusted under 35 U.S.C. 154(b) by 0 days.

(21) Appl. No.: 16/436,416

(22) Filed: Jun. 10, 2019

(65) Prior Publication Data

US 2019/0314462 A1 Oct. 17, 2019

Related U.S. Application Data

(62) Division of application No. 15/119,922, filed as application No. PCT/JP2015/055070 on Feb. 23, 2015, now abandoned.

(30) Foreign Application Priority Data

Feb. 21, 2014 (JP) .............................. JP2014-032313
Jul. 31, 2014 (JP) .............................. JP2014-157145
Sep. 17, 2014 (JP) .............................. JP2014-189487

(51) Int. Cl.
| | |
|---|---|
| A61K 38/47 | (2006.01) |
| A61K 9/16 | (2006.01) |
| A61K 9/20 | (2006.01) |
| A61K 9/00 | (2006.01) |
| C12N 7/00 | (2006.01) |
| C12N 9/36 | (2006.01) |

(52) U.S. Cl.
CPC ............ *A61K 38/47* (2013.01); *A61K 9/0014* (2013.01); *A61K 9/1623* (2013.01); *A61K 9/2018* (2013.01); *C12N 7/00* (2013.01); *C12N 9/2462* (2013.01); *C12Y 302/01017* (2013.01); *C12N 2770/16063* (2013.01)

(58) Field of Classification Search
CPC .... A61K 38/47; A61K 9/1623; A61K 9/2018; A61K 9/0014; C12N 7/00; C12N 9/2462; C12N 2770/16063; C12Y 302/01017; A61P 31/14

See application file for complete search history.

(56) References Cited

U.S. PATENT DOCUMENTS

| | | |
|---|---|---|
| 4,670,178 A | 6/1987 | Huth et al. |
| RE32,672 E | 5/1988 | Huth |
| 5,630,884 A | 5/1997 | Huth |
| 6,099,835 A | 8/2000 | Kiczka |
| 2005/0008631 A1 | 1/2005 | Lee-Huang et al. |
| 2007/0191255 A1 | 8/2007 | Vunk et al. |
| 2010/0240600 A1 | 9/2010 | Shimamoto et al. |
| 2013/0023582 A1 | 1/2013 | Shimamoto et al. |
| 2017/0049863 A1 | 2/2017 | Takahashi et al. |

FOREIGN PATENT DOCUMENTS

| | | |
|---|---|---|
| CN | 86106181 A | 6/1987 |
| CN | 101384176 A | 3/2009 |
| CN | 101461379 A | 6/2009 |
| CN | 101730536 A | 6/2010 |
| JP | S63-52867 A | 3/1988 |
| JP | 2-2329 A | 1/1990 |
| JP | 3-504121 A | 9/1991 |
| JP | 5-221875 A | 8/1993 |
| JP | 6-246157 A | 9/1994 |

(Continued)

OTHER PUBLICATIONS

Chinese Office Action and Search Report dated Mar. 28, 2019 in the counterpart application CN2015800093282; with English machine translation (total 23 pages) (D2, U.S. Pat. No. 6,099,835, D3, JPH08-27027, D5, JP2008-187954, D6, U.S. Pat. No. 5,630,884, D7, WO02/04011, D9, JP2007-312740, D10, Ibrahim 1996, and D11, Nohara 1999 cited in the Chinese Office Action are not listed in this IDS since they were already listed in the IDS filed Jun. 10, 2019).

Nakazawa et al., "The mechanism of the anti-viral effect of the modified lysozyme" Abstracts of the Meeting of the Food Hygiene Society of Japan, vol. 108, Dec. 2014, p. 66; w/ English machine translation (cited in the ISR of parent; cited in the ISR of related application PCT/JP2015/071726 (WO2016/017784)).

(Continued)

*Primary Examiner* — Renee Claytor
*Assistant Examiner* — Susan E. Fernandez
(74) *Attorney, Agent, or Firm* — Westerman, Hattori, Daniels & Adrian, LLP

(57) ABSTRACT

Provided is a norovirus deactivator, including a lysozyme component that includes at least one kind selected from lysozyme and/or a salt thereof, and a denatured product thereof.

5 Claims, 5 Drawing Sheets

(56) References Cited

FOREIGN PATENT DOCUMENTS

| | | | |
|---|---|---|---|
| JP | 8-27027 A | 1/1996 | |
| JP | 2004-505616 A | 2/2004 | |
| JP | 2007-300831 A | 11/2007 | |
| JP | 2007-312740 A | 12/2007 | |
| JP | 2008-187954 A | 8/2008 | |
| JP | 5092145 B2 | 12/2012 | |
| JP | 2013-47196 A | 3/2013 | |
| JP | 58-6434 B1 | 11/2015 | |
| WO | 98/51334 A1 | 11/1998 | |
| WO | 02/04011 A1 | 1/2002 | |
| WO | 2007/098032 A2 | 8/2007 | |
| WO | 2008/153077 A1 | 12/2008 | |
| WO | WO-2013009678 A2 * | 1/2013 | .............. A61P 31/14 |
| WO | 2015/125961 A1 | 8/2015 | |
| WO | 2016/017784 A1 | 2/2016 | |

OTHER PUBLICATIONS

Ibrahim et al., "Partially Unfolded Lysozyme at Neutral pH Agglutinates and Kills Gram-Negative and Gram-Positive Bacteria through Membrane Damage Mechanism", J. Agric. Food Chem., vol. 44, 1996, pp. 3799-3806 (in English; cited in the ISR of related application PCT/JP2015/071726 (WO2016/017784) (p. 3799, right col., line 13 to p. 3800, left col., line 13, p. 3802 "Structural Properties of Denaturated Lysozyme", Fig. 4)).

Kocherbitov et al., "Hydration of Thermally Denatured Lysozyme Studied by Sorption Calorimetry and Differential Scanning Calorimetry", J. Phys. Chem. B., vol. 110, 2016, pp. 10144-10150 (in English; cited in the ISR of related application PCT/JP2015/071726 (WO2016/017784) (p. 10145, col. "Materials and Methods", lines 1-10).

Takahashi et al., "Heat-Denatured Lysozyme Inactivates Murine Norovirus as a Surrogate Human Norovirus", Scientific Reports, Jul. 2, 2015, pp. 1-9 (in English; cited in the ISR of related application PCT/JP2015/071726 (WO2016/017784) (entire text); cited in the Singapore Search Report and Written Opinion dated Jan. 24, 2018; cited in the Chinese Office Action dated Oct. 26, 2018).

International Search Report and Written Opinion dated Mar. 31, 2015 issued in parent's corresponding application No. PCT/JP2015/055070; w/ English partial translation and partial machine translation (17 pages).

International Preliminary Report on Patentability dated Feb. 9, 2017 in related application No. PCT/JP2015/071726 (WO2016017784A1) (corresponding to Japanese application No. 2014-157145 whose priority is claimed in this application); English translation (14 pages).

European Supplemental Search Report and Written Opinion dated Oct. 20, 2017 in corresponding European application No. 15751488.6; in English (6 pages).

Singapore Search Report and Written Opinion dated Jan. 24, 2018 in corresponding Singapore application No. 11201700611T; in English (13 pages).

Chinese Office Action dated Oct. 26, 2018 in corresponding application No. CN 201580041459.9; with English machine translation (19 pages).

Hayakawa et al., "Contribution of Hydrophobicity, Net Charge and Sulfhydryl Groups to Thermal Properties of Ovalbumin", Can. Inst. Food Sci. Technol. J., vol. 18, No. 4, pp. 290-295 (1985) (in English; cited in the Chinese Office Action dated Oct. 26, 2018).

Ibrahim et al., "A structural phase of heat-denatured lysozyme with novel antimicrobial action", J. Agric. Food Chem., vol. 44, 1996, pp. 1416-1423 (in English; cited in the Office Action dated Apr. 16, 2018 in parent).

Nohara et al., "Kinetic study on thermal denaturation of hen egg-white lysozyme involving precipitation", J. of Bioscience and Bioengineering, vol. 87, 1999, No. 2, pp. 199-205 (in English; cited in the Office Action dated Jan. 10, 2019 in parent).

Ray et al., "An electrospray ionization mass spectrometry investigation of 1-anilino-8-naphtalene-sulfonate (ANS) binding to proteins", J. Am. Soc. Mass Spectrom., vol. 12, 2001, pp. 428-438 (in English; cited in the Office Action dated Jan. 10, 2019 in parent).

Japanese Office Action dated Sep. 3, 2019 in counterpart application JP 2016-538455; with English machine translation (total 15 pages) (D1-D6 and D8-D9 cited in the Japanese Office Action are not listed in this IDS since they were already listed in the IDS filed Jun. 10, 2019).

Hitachi, "What is fluorescence", https://www.hitachi-hightech.com/hhs/products/tech/ana/uv/fl_basic/fluorescence.html, Aug. 23, 2019; with English version Oct. 4, 2019 (total 15 pages) (D10 cited in the Japanese Office Action dated Sep. 3, 2019).

Chinese Office Action dated Jul. 15, 2019 in counterpart application CN 201580041459; with English machine translation (total 17 pages).

Yang Man-Ii et al., "Study on antimicrobial properties and structure of chemical modified lysozyme", Food and Fermentation Industries, Jun. 21, 2016, pp. 22-26; with English abstract and machine translation (total 13 pages).

Cisani et al., "Inhibition of Herpes Simplex Virus-induced Cytopathic Effect by Modified Hen Egg-white Lysozymes", Current Microbiology, vol. 10, 1984, pp. 35-40 (in English, cited in Office Action dated Jun. 15, 2021, issued in counterpart Korean Patent Application No. 10-2016-7024237).

Notice of Allowance dated Nov. 5, 2020, issued in counterpart Chinese Application No. 201580009328.2 (w/ English translation; 6 pages).

\* cited by examiner

NOROVIRUS (ALONE)

LYSOZYME DENATURED PRODUCT
(HEATING OF 80°C × 180 MINUTES)

NOROVIRUS AND LYSOZYME
DENATURED PRODUCT
(HEATING OF 80°C × 180 MINUTES)
(TIME POINT OF 1 MINUTE FROM
START OF CONTACT)

NOROVIRUS AND LYSOZYME
DENATURED PRODUCT
(HEATING OF 80°C × 180 MINUTES)
(TIME POINT OF 1 HOUR FROM START
OF CONTACT)

NOROVIRUS AND UNHEATED LYSOZYME
(TIME POINT OF 1 MINUTE FROM
START OF CONTACT)

NOROVIRUS DEACTIVATOR AND METHOD FOR PRODUCING SAME, METHOD FOR DEACTIVATING NOROVIRUS, METHOD FOR PRODUCING LYSOZYME COMPONENT FOR NOROVIRUS DEACTIVATION USE, PROPHYLACTIC OR THERAPEUTIC AGENT FOR NOROVIRUS INFECTION, AND EXTERNAL PREPARATION FOR SKIN FOR NOROVIRUS DEACTIVATION PURPOSES

This application is a divisional of U.S. application Ser. No. 15/119,922 filed Aug. 18, 2016, which is a national stage of PCT/JP2015/055070 filed Feb. 23, 2015, each of which is hereby incorporated by reference herein in its entirety.

TECHNICAL FIELD

The present invention relates to a norovirus deactivator including at least one kind of lysozyme and/or a salt thereof, and a denatured product thereof and a method of producing the same, a method of deactivating norovirus, a method of producing a lysozyme component for norovirus deactivation use, a prophylactic agent or therapeutic agent for norovirus infection, and an external preparation for skin for norovirus deactivation purposes.

BACKGROUND ART

Norovirus is highly infectious to humans, and causes food poisoning and acute viral gastroenteritis (infectious disease). At present, there is no vaccine for norovirus, and there is also no effective antiviral agent. Accordingly, once the infection is developed, its treatment is limited to symptomatic therapy like infusion. Consequently, the symptom becomes severe in an elderly patient or the like in some cases.

A main infection pathway of norovirus is oral infection. Accordingly, in order to prevent an onset of the food poisoning or the infectious disease and to prevent spread after the onset, it is extremely important to deactivate norovirus present in an environment.

Hitherto, many disinfectants, such as alcohol preparations, have been considered ineffective for deactivation of norovirus, and for the purpose of deactivation, heating at 85° C. for 1 minute or more or treatment with sodium hypochlorite has been recommended. However, practical use of sodium hypochlorite is limited because of its corrosive action on metal, irritating action on skin, and bleaching action on, for example, clothing. Accordingly, there is a demand for development of an alternative deactivator to sodium hypochlorite.

To that end, as an active ingredient of a norovirus deactivator, there have been proposed, for example, a persimmon tannin extract (persimmon tannin) (Patent Literature 1), and proanthocyanidin contained in grape seeds or the like (Patent Literature 2).

Specifically, in Patent Literature 1, there is a disclosure that application of the persimmon tannin extract for 2 minutes exhibited inhibition rates of from 86% to 99% for viral genome RNA counts, and in Patent Literature 2, there is a disclosure that proanthocyanidin had an infectivity titer (log $TCID_{50}$/mL) of 3 with respect to a control in a $TCID_{50}$ method in the case of an action time of 1 minute. However, in any of those cases, sufficient deactivation of norovirus has not been achieved, and in view of strong infectivity of norovirus, there is a demand for development of a novel deactivator having a stronger deactivating effect.

CITATION LIST

Patent Literature

[PTL 1] JP 5092145 B2
[PTL 2] JP 2013-047196 A

SUMMARY OF INVENTION

Technical Problem

It is an object of the present invention to provide a technology for effectively deactivating norovirus.

Solution to Problem

The inventors of the present invention have surprisingly found that at least one kind of lysozyme and/or a salt thereof, and a denatured product thereof has an excellent deactivating action on norovirus. Thus, the inventors have arrived at the present invention.

1. A norovirus deactivator according to one embodiment of the present invention includes a lysozyme component that includes at least one kind selected from lysozyme and/or a salt thereof, and a denatured product thereof.

2. In the norovirus deactivator according to the above-mentioned item 1, a content of the lysozyme component may be 0.05 mass % or more.

3. In the norovirus deactivator according to the above-mentioned item 1 or 2, the lysozyme component may have a fluorescence intensity specified by the following definition of 4,000 or more:

Fluorescence intensity: a fluorescence intensity measured under conditions of an excitation wavelength of 390 nm with an excitation bandwidth of 10 nm, a fluorescence wavelength of 470 nm with a fluorescence band width of 10 nm for a liquid obtained by adding 25 µL of a methanol solution of 8 mM 1,8-anilinonaphthalenesulfonic acid to 5 mL of a dilution obtained by diluting the lysozyme component with a phosphate buffer having a pH of 7.0 so as to have a concentration of the lysozyme component of 0.05 mass % in terms of solid content, and to have a concentration of phosphate of 0.2 M and then subjecting the liquid to a reaction at room temperature for 30 minutes.

4. In the norovirus deactivator according to any one of the above-mentioned items 1 to 3, the lysozyme component may have an anti-norovirus activity specified below of 2.0 or more:

Anti-norovirus activity: a value obtained by subtracting, when a norovirus mixed liquid obtained by mixing equal amounts of a norovirus solution and a 2 mass % aqueous solution of the lysozyme component is left standing at room temperature for 1 minute, a logarithm of an infectivity titer after the standing from a logarithm of an infectivity titer before the standing.

5. In the norovirus deactivator according to any one of the above-mentioned items 1 to 4, the norovirus deactivator may include a liquid formulation.

6. A method of deactivating norovirus according to one embodiment of the present invention may include deactivating norovirus using a lysozyme component that includes at least one kind selected from lysozyme and/or a salt thereof, and a denatured product thereof.

7. A method of producing a lysozyme component for norovirus deactivation use according to one embodiment of the present invention is a method of producing a lysozyme component for norovirus deactivation use to be incorporated into the norovirus deactivator of any one of the above-mentioned items 1 to 5, the method including thermally denaturing lysozyme and/or a salt thereof.

8. A method of producing a norovirus deactivator according to one embodiment of the present invention includes incorporating a lysozyme component that includes at least one kind selected from lysozyme and/or a salt thereof, and a denatured product thereof.

9. The method of producing a norovirus deactivator according to the one embodiment of the present invention is the method of producing a norovirus deactivator according to the above-mentioned item 8, further including: thermally denaturing the lysozyme and/or the salt thereof to obtain a thermally denatured product; and obtaining a norovirus deactivator containing the thermally denatured product.

10. In the method of producing a norovirus deactivator according to the above-mentioned item 9, obtaining the thermally denatured product may include:

a first heating step of heating an aqueous solution of the lysozyme and/or the salt thereof having a transmittance for light having a wavelength of 660 nm of more than 70%, a pH of 5.0 or more and 7.0 or less, and a concentration of the lysozyme and/or the salt thereof of 0.5 mass % or more and 7 mass % or less in terms of solid content, until the transmittance of the aqueous solution for light having a wavelength of 660 nm becomes 70%;

after the first heating step, a second heating step of heating the aqueous solution until the transmittance of the aqueous solution for light having a wavelength of 660 nm reaches a minimum of less than 70%, followed by heating of the aqueous solution until the transmittance becomes 70%; and after the second heating step, a third heating step of further heating the aqueous solution in a state in which the transmittance of the aqueous solution for light having a wavelength of 660 nm is more than 70%.

11. In the method of producing a norovirus deactivator according to the above-mentioned item 10, heating conditions of the third heating step may include such conditions that the heating is performed until a transmittance for light having a wavelength of 660 nm of a mixture of a product obtained by filtering the aqueous solution obtained in the third heating step through a 0.45 μm membrane filter with ethanol at a ratio of 1:1 in terms of mass ratio becomes 85% or more.

12. The method of producing a norovirus deactivator according to the above-mentioned item 10 or 11 may further include, after the third heating step, subjecting the aqueous solution to spray drying or freeze drying to obtain the denatured product in a powder form.

13. A prophylactic agent or therapeutic agent for norovirus infection according to one embodiment of the present invention includes a lysozyme component that includes at least one kind selected from lysozyme and/or a salt thereof, and a denatured product thereof.

14. An external preparation for skin for norovirus deactivation purposes according to one embodiment of the present invention includes a lysozyme component that includes at least one kind selected from lysozyme and/or a salt thereof, and a denatured product thereof.

15. A lysozyme component according to one embodiment of the present invention is a lysozyme component for norovirus deactivation use, including at least one kind selected from lysozyme and/or a salt thereof, and a denatured product thereof.

Advantageous Effects of Invention

The lysozyme component included in the norovirus deactivator of the present invention, which is at least one kind selected from the lysozyme and/or the salt thereof, and the denatured product thereof, has an excellent deactivating action on norovirus. In particular, the thermally denatured product can deactivate norovirus within an extremely short action time of 1 minute or less. In addition, hitherto, lysozyme has been used as a food additive for improving the shelf life of food, and lysozyme chloride has been used as an antiphlogistic. Accordingly, the norovirus deactivator of the present invention can be safely used. Therefore, the norovirus deactivator of the present invention, the method of deactivating norovirus of the present invention, the prophylactic agent or therapeutic agent for norovirus infection of the present invention, and the external preparation for skin for norovirus deactivation purposes of the present invention are useful for the inhibition of norovirus proliferation, the killing of norovirus, the prevention of norovirus infection, the prevention of the spread of the infection, and the treatment of the infection.

In particular, a norovirus deactivator obtained by mixing the lysozyme or the salt thereof, or the denatured product thereof with a liquid containing an alcohol, such as a lower alcohol or a polyhydric alcohol, exhibits both a sterilizing effect of the alcohol and a norovirus deactivating effect of the lysozyme component, and hence makes it possible to routinely sterilize a housing environment and deactivate norovirus.

In addition, according to the method of producing a norovirus deactivator of the present invention, the norovirus deactivator can be simply produced. Further, according to the method of producing a lysozyme component for norovirus deactivation use, a lysozyme component having an extremely high norovirus deactivating effect can be produced.

DESCRIPTION OF EMBODIMENTS

Figure 1:
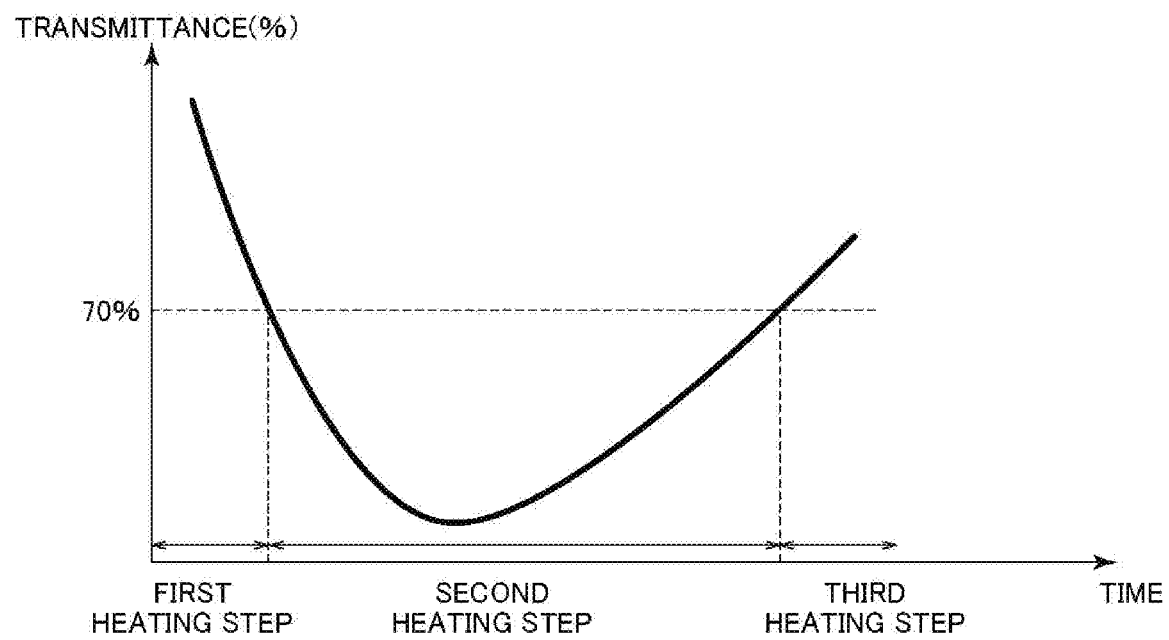
FIG. 1 is a graph for schematically showing a relationship between a heating time and a transmittance in a first heating step, a second heating step, and a third heating step in obtaining a thermally denatured product of lysozyme in a method of producing a norovirus deactivator of the present invention.

The present invention is hereinafter described in detail. In the present invention, "part(s)" means "part (s) by mass" and means "mass %" unless otherwise specified.

<Outline of Invention>

A norovirus deactivator of the present invention includes at least one kind selected from lysozyme and/or a salt thereof, and a denatured product thereof (hereinafter sometimes abbreviated as "lysozyme component"). The lysozyme component is used for the deactivation of norovirus. That is, the norovirus deactivator of the present invention may include one kind or two or more kinds of lysozyme and/or a salt thereof, and a denatured product thereof (the denatured product of the lysozyme and/or the salt thereof is hereinafter sometimes abbreviated as "lysozyme denatured product").

For example, the norovirus deactivator of the present invention may use the lysozyme component (e.g., the lysozyme or the salt thereof, or the denatured product thereof) as an active ingredient. Such norovirus deactivator may be used as, for example, a disinfectant for norovirus, or a prophylactic agent or therapeutic agent for norovirus infection. In addition, depending on its use form, the norovirus deactivator may be used as any of an external preparation and an oral preparation.

In the present invention, the "deactivation of (to deactivate) norovirus" refers to a decrease in activity of norovirus which causes symptoms, such as vomiting and diarrhea, by infecting epithelial cells of the small intestine to proliferate, and includes not only a decrease in activity by the killing of norovirus, but also a decrease in only the activity in a state in which norovirus is viable.

<Lysozyme and/or Salt Thereof>

In the present invention, the "lysozyme" refers to a protein having a property of hydrolyzing a β-1,4 bond between N-acetylglucosamine and N-acetylmuramic acid.

The lysozyme that may be incorporated into the norovirus deactivator of the present invention is widely present in the biological world, such as eggs, animal tissues, body fluids, and plants, and is broadly classified into the following five kinds of families on the basis of substrate specificity and structure. In addition, the lysozyme and/or the salt thereof may be used as a raw material for the lysozyme denatured product.

1. Lysozymes (bacterium type)
2. Lysozymes (chicken type)
3. Lysozymes (goose type)
4. Lysozymes (phage type; type V)
5. Lysozymes (CH type)

In the present invention, any of the five kinds of families may be used. Of those lysozymes, as the lysozyme component to be used in the present invention, and as a raw material for the lysozyme denatured product, lysozymes (chicken type), such as egg white lysozyme and human lysozyme, are preferred from the viewpoint of their wide use as food additives and the like. Further, egg white lysozyme and/or a denatured product thereof is particularly preferred because of the low cost and easy availability thereof.

In addition, examples of the salt of the lysozyme include salts that are acceptable as food additives or pharmaceutically acceptable salts, for example, salts of inorganic acids, such as hydrochloric acid, carbonic acid, phosphoric acid, boric acid, hexametaphosphoric acid, nitric acid, and sulfuric acid, and salts of organic acids, such as citric acid, tartaric acid, succinic acid, malic acid, acetic acid, glutamic acid, glycerophosphoric acid, and gluconic acid. Of the salts of the lysozyme, salts of inorganic acids are preferred, and hydrochloric acid salts, such as lysozyme chloride, are more preferred because of their wide use as antiphlogistics and established safety.

As a method of denaturing the lysozyme and/or the salt thereof, there may be given, for example, heat treatment, acid treatment, alkali treatment, enzyme treatment, organic solvent treatment, surfactant treatment, oxidation treatment, reduction treatment, and high-pressure treatment. One of those denaturation treatments may be performed alone, or two or more thereof may be performed in combination. The lysozyme denatured product also encompasses a lysozyme-derived peptide obtained by subjecting the lysozyme and/or the salt thereof to decomposition treatment.

Of the lysozyme components, one obtained by thermally denaturing the lysozyme and/or the salt thereof (hereinafter sometimes referred to simply as "thermally denatured product") is preferred in terms of its deactivating effect on norovirus. The thermally denatured product can deactivate norovirus within a short period of time as compared to unheated lysozyme and/or a salt thereof. In view of this, the present invention also encompasses, as a method of producing lysozyme for norovirus deactivation use, a method of thermally denaturing lysozyme and/or a salt thereof.

Heating conditions of the thermal denaturation are not particularly limited as long as the denaturation of the lysozyme and/or the salt thereof is appropriately performed, but it is preferred to heat the lysozyme and/or the salt thereof at 50° C. or more and 130° C. or less, preferably 60° C. or more, more preferably 70° C. or more.

As a method for the thermal denaturation, the lysozyme and/or the salt thereof may be heated after being dissolved in a solvent, or may be heated as powder. When the lysozyme and/or the salt thereof is heated after being dissolved, the heating time, which may be determined depending on the heating temperature of the lysozyme, may be 1 minute or more and 720 minutes or less. When the lysozyme and/or the salt thereof is heated as powder, the heating time is preferably 1 day or more and less than 30 days. The solvent is not limited as long as the solvent is capable of dissolving the lysozyme and/or the salt thereof, and the solvent may be, for example, water or a water-containing organic solvent.

<Obtaining Thermally Denatured Product>

The obtaining the thermally denatured product includes: a first heating step of heating an aqueous solution of lysozyme having a transmittance for light having a wavelength of 660 nm of more than 70% (preferably 80% or more, more preferably 90% or more, and generally 100% or less), a pH of 5.0 or more and 7.0 or less, and a concentration of the lysozyme and/or the salt thereof of 0.5 mass % or more and 7 mass % or less in terms of solid content, until the transmittance of the aqueous solution for light having a wavelength of 660 nm becomes 70% (hereinafter sometimes referred to simply as "first heating step"); after the first heating step, a second heating step of heating the aqueous solution until the transmittance of the aqueous solution for light having a wavelength of 660 nm reaches a minimum of less than 70%, followed by heating of the aqueous solution until the transmittance becomes 70% (hereinafter sometimes referred to simply as "second heating step"); and after the second heating step, a third heating step of further heating the aqueous solution in a state in which the transmittance of the aqueous solution for light having a wavelength of 660 nm is more than 70% (hereinafter sometimes referred to simply as "third heating step"). Through the first heating step, the second heating step, and the third heating step, the lysozyme denatured product can be obtained.

Through the first heating step, the second heating step, and the third heating step, a lysozyme denatured product having a fluorescence intensity specified by the above-mentioned definition of 4,000 or more can be obtained.

[Mechanism of Heating]

FIG. 1 is a graph for schematically showing a relationship between a heating time and a transmittance in the first heating step, the second heating step, and the third heating step in a method of producing a lysozyme denatured product according to one embodiment of the present invention. The inventors of the present invention have found that in the heating of an aqueous solution containing lysozyme, its transmittance for light having a wavelength of 660 nm is changed in accordance with the heating time as shown in FIG. 1. The change in transmittance is presumed to result from a change in surface hydrophobicity of the lysozyme denatured product to be obtained (mainly an increase in surface hydrophobicity) and a change in water solubility of the lysozyme denatured product (a decrease in water solubility and a subsequent increase in water solubility).

[First Heating Step]

As shown in FIG. 1, the fact that in the aqueous solution having a transmittance for light having a wavelength of 660 nm of more than 70%, the transmittance for the light is decreased to 70% through the first heating step means that the transmittance of the aqueous solution is decreased, and for example, clouding of the aqueous solution may be found through visual observation.

That is, in the first heating step, the transmittance of the aqueous solution for light having a wavelength of 660 nm is decreased from more than 70% to 70% presumably as a result of the following: the three-dimensional structure of the lysozyme and/or the surface hydrophobicity of the surface of the lysozyme in the aqueous solution is increased, and the lysozyme is aggregated through attraction between hydrophobic portions to have decreased solubility in the aqueous solution.

(Raw Material)

As the lysozyme and/or the salt thereof serving as the raw material, to be used in the aqueous solution in the first heating step, the lysozyme and/or the salt thereof exemplified in the foregoing section <Lysozyme and/or Salt thereof> may be used. The lysozyme and/or the salt thereof serving as the raw material is preferably egg white lysozyme because of its low cost and easy availability.

(Concentration of Raw Material)

In the first heating step, the concentration of the lysozyme in the aqueous solution is preferably 1 mass % or more and is preferably 5 mass % or less because the three-dimensional structure of the lysozyme can be reliably changed and aggregation of the lysozyme can be prevented to enhance its deactivating action on norovirus.

(Aqueous Solution of Lysozyme and/or Salt Thereof)

A solvent for forming the aqueous solution of the lysozyme and/or the salt thereof is water, but there may be used an organic solvent that is miscible with water as long as the solubility of the lysozyme and/or the salt thereof in water is not affected. The ratio of water in the solvent for forming the aqueous solution of the lysozyme and/or the salt thereof is generally 80 mass % or more and 100 mass % or less. In addition, when the solvent for forming the aqueous solution of the lysozyme and/or the salt thereof contains the organic solvent that is miscible with water, the ratio of the organic solvent in the solvent for forming the aqueous solution of the lysozyme and/or the salt thereof is generally 1 mass % or more and 20 mass % or less.

The organic solvent only needs to be an organic solvent that is miscible in water, and examples thereof include alcohol-based solvents, such as methanol, ethanol, 1-propanol, 2-propanol, ethylene glycol, propylene glycol, and glycerin; ketone-based solvents, such as acetone and methyl ethyl ketone; acetonitrile; tetrahydrofuran; and 1,4-dioxane. Those organic solvents may each be used alone, or two or more kinds thereof may be used in combination.

(pH)

In each of the first heating step, the second heating step, and the third heating step, the pH of the aqueous solution is more preferably 5.5 or more and is more preferably 6.5 or less because aggregation of the lysozyme can be prevented and the surface hydrophobicity of the lysozyme denatured product to be obtained can be increased.

In addition, as required, any of the following may be used to adjust the aqueous solution to have a pH within the above-mentioned range: acids (e.g., inorganic acids, such as hydrochloric acid, sulfuric acid, and nitric acid, and organic acids, such as citric acid, acetic acid, and phosphoric acid), alkalis (e.g., inorganic bases, such as sodium hydroxide and potassium hydroxide), and buffers (e.g., acetate buffer).

For example, when the lysozyme is the salt of lysozyme (e.g., lysozyme chloride), the first heating step is preferably performed after adjusting the pH of the aqueous solution to a pH within the above-mentioned range with an acid, an alkali, or a buffer.

[Second Heating Step]

In the second heating step, the aqueous solution obtained in the first heating step is heated until its transmittance for light having a wavelength of 660 nm reaches, from 70%, a minimum of less than 70% (preferably less than 60%, more preferably less than 50%, and generally 0% or more), and then heated until the transmittance becomes 70%. Thus, the light transmittance of the aqueous solution obtained in the first heating step is further decreased (as a result, clouding and/or precipitation in the aqueous solution may be found by visual observation). After that, the transmittance starts to be increased, and gradual disappearance of the clouding and/or the precipitation (as a result, it may be found by visual observation that the aqueous solution gradually becomes transparent) may be found.

That is, in the second heating step, the transmittance of the aqueous solution for light having a wavelength of 660 nm becomes 70% presumably as a result of the following: as the three-dimensional structure of the lysozyme in the aqueous solution is further changed to further increase the surface hydrophobicity of the lysozyme, the water solubility of the lysozyme is temporarily decreased and is then increased.

A mechanism by which as the surface hydrophobicity of the lysozyme is further increased in the second heating step, the water solubility of the lysozyme is temporarily decreased and is then increased has yet to be elucidated, but this is presumably because through the second heating step, the lysozymes aggregated in the first heating step are bound to be changed into a linear aggregate, and the aggregate is dissolved in the aqueous solution, resulting in an increase in solubility of the lysozyme in the aqueous solution.

The second heating step may be performed after the first heating step without any interruption. That is, the second heating step may be performed successively after the first heating step.

[Third Heating Step]

In the third heating step, the transmittance of the aqueous solution for light having a wavelength of 660 nm can keep a value of more than 70% presumably as a result of the following: the three-dimensional structure of the lysozyme in the aqueous solution is further changed to further increase the surface hydrophobicity of the lysozyme in a state in which the water solubility of the lysozyme is kept.

More specifically, in the third heating step, it is preferred that clouding and/or precipitation not occur in the aqueous solution (the transmittance (transparency) of the aqueous solution be kept).

In the third heating step, the heating is more preferably performed until the transmittance of the aqueous solution for light having a wavelength of 660 nm becomes 75% or more, more preferably 80% or more (generally 100% or less) because the three-dimensional structure of the lysozyme in the aqueous solution can be more reliably changed.

Further, in the third heating step, the heating is preferably performed until the transmittance for light having a wavelength of 660 nm of a mixture of a product obtained by filtering the aqueous solution obtained in the third heating step through a 0.45 μm membrane filter with ethanol at a ratio of 1:1 in terms of mass ratio becomes 85% or more, more preferably 90% or more (generally 100% or less).

The fact that the transmittance for light having a wavelength of 660 nm of the mixture of the product obtained by filtering the aqueous solution obtained in the third heating step through a 0.45 μm membrane filter with ethanol at a ratio of 1:1 in terms of mass ratio becomes 85% or more may be used as an index of the fact that a lysozyme denatured product having a fluorescence intensity specified by the above-mentioned definition of 4,000 or more has been obtained.

The third heating step may be performed after the second heating step without any interruption. That is, the third heating step may be performed successively after the first heating step and the second heating step.

In the third heating step, the aqueous solution heated in a state in which the transmittance is more than 70% (made transparent) can keep the transmittance (can keep transparency) even when returned to room temperature (e.g., 25° C.). This is presumably because the form (three-dimensional structure) of the lysozyme or the like contained in the aqueous solution is kept even at room temperature.

(Heating Temperature and Heating Time)

In the method of producing a norovirus deactivator (production of a lysozyme denatured product) according to this embodiment, the heating is preferably performed so that the aqueous solution in each of the first heating step, the second heating step, and the third heating step has a product center temperature of 70° C. or more because high yield can be achieved and the aqueous solution can be adjusted to the transmittance specified in each of the first heating step, the second heating step, and the third heating step. In addition, the product center temperature is more preferably 80° C. or more, still more preferably 90° C. or more (may be 130° C. or less, may be about 100° C. or less) because the production time can be shortened by virtue of a short heating time. The heating time in each of the first heating step, the second heating step, and the third heating step may be appropriately determined so as to satisfy the transmittance specified in each of the steps depending on the heating temperature and treatment amount.

When the first heating step, the second heating step, and the third heating step are successively performed at the same heating temperature, the total of the heating times in the first heating step, the second heating step, and the third heating step is preferably as follows: when the product center temperature is 70° C. or more and 75° C. or less, 125 minutes or more and 720 minutes or less; when the product center temperature is more than 75° C. and 80° C. or less, 80 minutes or more and 435 minutes or less; when the product center temperature is more than 80° C. and 85° C. or less, 70 minutes or more and 305 minutes or less; when the product center temperature is more than 85° C. and 90° C. or less, 50 minutes or more and 240 minutes or less; when the product center temperature is more than 90° C. and 95° C. or less, 40 minutes or more and 185 minutes or less; when the product center temperature is more than 95° C. and 100° C. or less, 25 minutes or more and 120 minutes or less; and when the product center temperature is more than 100° C., 10 minutes or more and 120 minutes or less.

(Spray Drying/Freeze Drying)

The method of producing a lysozyme denatured product of the present invention may further include, after the third heating step, subjecting the aqueous solution to spray drying or freeze drying to obtain the lysozyme denatured product in a powder form.

The spray drying and the freeze drying may each be performed in accordance with an ordinary method.

<Norovirus Deactivating Action>

In the present invention, a norovirus deactivating action may be evaluated by a system using a method described later in Examples (that is, murine cells infected with norovirus).

(Fluorescence Intensity)

In the lysozyme component of the present invention, the lysozyme component (denatured product of the lysozyme and/or the salt thereof (hereinafter sometimes referred to as "lysozyme denatured product"), more specifically, the lysozyme denatured product has a fluorescence intensity specified by the following definition of preferably 4,000 or more, more preferably 5,000 or more, and generally 10,000 or less because higher surface hydrophobicity and a more excellent deactivating action on norovirus are obtained. In the present invention, the "room temperature" refers to 20° C. or more and 25° C. or less.

Fluorescence intensity: a fluorescence intensity measured under conditions of an excitation wavelength of 390 nm with excitation band width: 10 nm and a fluorescence wavelength of 470 nm with fluorescence band width: 10 nm for a liquid obtained by adding 25 μL of a methanol solution of 8 mM 1,8-anilinonaphthalenesulfonic acid to 5 mL of a dilution obtained by diluting the lysozyme component with a phosphate buffer (pH 7.0) so as to have a concentration of the lysozyme component of 0.05 mass % in terms of solid content, and to have a concentration of phosphate of 0.2 M and then subjecting the liquid to a reaction at room temperature for 30 minutes.

The fluorescence intensity of the lysozyme component specified in the present invention is an index of the surface hydrophobicity of the lysozyme component. That is, as the fluorescence intensity of the lysozyme component specified in the present invention becomes higher, the surface hydrophobicity of the lysozyme component may be said to be higher. In addition, as the surface hydrophobicity of the lysozyme component becomes higher, its deactivating effect on norovirus (anti-norovirus activity) tends to be more excellent.

The inventors of the present invention have found that as the surface hydrophobicity of the lysozyme component becomes higher, its deactivating action on norovirus tends to be higher. Of those, a lysozyme denatured product of the present invention that is a lysozyme processed product and/or a salt thereof has a feature of having a more excellent deactivating action on norovirus. In the present invention, the "lysozyme processed product" refers to a lysozyme denatured product that has a three-dimensional structure different from that of the lysozyme and/or the salt thereof.

Although the causes for the lysozyme processed product and/or the salt thereof of the present invention to have an excellent deactivating action on norovirus have yet to be elucidated, it is presumed that: first, the lysozyme processed product and/or the salt thereof having surface hydrophobicity easily binds to the hydrophobic site of norovirus; secondly, the lysozyme processed product and/or the salt thereof is a lysozyme denatured product, the lysozyme processed product contains thiol groups (—SH) obtained by the cleavage of at least part of S—S bonds of lysozyme as a result of denaturation, and the thiol groups are bonded to S—S bonds present on the surface of norovirus; and thirdly, the lysozyme processed product and/or the salt thereof has a three-dimensional structure that easily binds to norovirus.

Diluting the lysozyme component with a phosphate buffer so as to have a concentration of the lysozyme component of 0.05 mass % in terms of solid content, and to have a concentration of phosphate of 0.2 M specifically refers to, in the case of, for example, measuring the fluorescence intensity of an aqueous solution containing the lysozyme component at 1 mass % in terms of solid content, putting 5 g of the aqueous solution and 80 mL of a 0.25 M phosphate buffer into a 100 mL volumetric flask, and then making an adjustment by adding purified water to a total volume of 100 mL.

In the present invention, the fluorescence intensity of the lysozyme component is a value measured by a method described in Canadian Institute of Food Science and Technology 1985 Vol. 18 No. 4, p. 290-295. The phosphate buffer to be used in the measurement of the fluorescence intensity of the lysozyme component in the present invention is one prepared using sodium dihydrogen phosphate and disodium hydrogen phosphate. In addition, the fluorescence intensity of the lysozyme component in the present invention is a value obtained by separately measuring, as a blank value, the fluorescence intensity of a 0.2 M phosphate buffer (pH 7.0, containing sodium dihydrogenphosphate and disodium hydrogen phosphate as phosphates), and subtracting the blank value.

More specifically, the fluorescence intensity of the lysozyme component is a value when measured using a fluorescence spectrophotometer available under the model name FP-8500 from JASCO Corporation under the conditions of an excitation wavelength of 390 nm with an excitation bandwidth of 10 nm, a fluorescence wavelength of 470 nm with a fluorescence band width of 10 nm, a response of 0.5 sec, low sensitivity (about 270±10 V) (power supply frequency (50/60 Hz)), and using a peristaltic sipper SHP-820 model. Measurement may be performed using any other fluorescence spectrophotometer (e.g., a fluorescence spectrophotometer available under the model name F-2000 from Hitachi, Ltd.). In that case, measurement conditions, such as sensitivity, need to be conformed to the conditions specified in the present application.

(Anti-Norovirus Activity)

The lysozyme component preferably has an anti-norovirus activity specified below of 2.0 or more.

Anti-norovirus activity: a value obtained by subtracting, when a norovirus mixed liquid obtained by mixing equal amounts of a norovirus solution and a 2 mass % aqueous solution of the lysozyme component is left standing at room temperature for 1 minute, a logarithm of an infectivity titer after the standing from a logarithm of an infectivity titer before the standing.

(Dimer and Trimer)

The lysozyme component (the lysozyme denatured product, more specifically, the lysozyme processed product and/or the salt thereof) may contain an about 29 KDa (KDa=$10^3$ Da) protein and/or an about 36.5 KDa protein. That is, the norovirus deactivator of the present invention may include the about 29 KDa protein and/or the about 36.5 KDa protein. Whether or not each of the norovirus deactivator of the present invention and the lysozyme component includes the about 29 KDa protein and/or the about 36.5 KDa protein may be determined by electrophoresis described later in Examples. The electrophoresis may be performed using a commercially available electrophoresis kit.

The about 29 KDa protein is presumed to be a dimer of the lysozyme denatured product, and the about 36.5 KDa protein is presumed to be a trimer of the lysozyme denatured product.

The anti-norovirus activity of the norovirus deactivator of the present invention is enhanced by virtue of including the about 29 KDa protein and/or the about 36.5 KDa protein.

<Content of Lysozyme and/or Salt Thereof>

The preferred content (in terms of solid content) of the lysozyme component in the norovirus deactivator of the present invention depends on, for example, the kind of the lysozyme to be used in the norovirus deactivator, and the dosage form and use mode of the norovirus deactivator, but may be set to 0.05 mass % or more, further 0.1 mass % or more, particularly 0.25 mass % or more (for example, 0.05 mass % or more and 100 mass % or less) of the norovirus deactivator. Herein, when the norovirus deactivator of the present invention includes two or more kinds of lysozyme components, the content of the lysozyme component (in terms of solid content) refers to the total content of the lysozyme components.

<Formulation Material>

In the norovirus deactivator of the present invention, a formulation material that is formulated with the lysozyme component may be appropriately selected depending on, for example, the dosage form of the norovirus deactivator. For example, the following materials may be appropriately used in combination: water; a lower alcohol having 5 or less carbon atoms, such as ethanol or isopropanol; a polyhydric alcohol, such as glycerin, polyethylene glycol, butylene glycol, propylene glycol, dipropylene glycol, or sorbitol; a bacteriostatic agent, such as glycine, an organic acid, a glycerol fatty acid ester, a sucrose fatty acid ester, sodium benzoate, sodium sorbate, sodium propionate, sodium dehydroacetate, a paraoxybenzoic acid ester, sodium sulfite, EDTA, benzalkonium chloride, benzethonium chloride, chlorhexidine gluconate, an alkyldiaminoethylglycine hydrochloride, iodine tincture, povidone iodine, benzalkonium cetyl phosphate, triclosan, chloroxylenol, isopropyl methylphenol, ε-polylysine, lactoferrin, nisin, bacteriocin, *Aralia cordata* extract, *Styrax japonica* extract, *Artemisia capillaris* extract, enzymatically hydrolyzed coix extract, milt protein extract, thujaplicin, or a pectin digest.

Of those, through the use of at least one kind of water, a lower alcohol, and a polyhydric alcohol, in particular, through the use of an alcohol preparation containing at least one kind of a lower alcohol and a polyhydric alcohol, the norovirus deactivator can have both a sterilizing effect of the alcohol and a norovirus deactivating effect of the lysozyme component, and hence has increased usefulness as a disinfectant.

Further, the norovirus deactivator of the present invention may contain, as required, any of additives including a pH adjuster, such as citric acid, sodium citrate, sodium hydroxide, or triethanolamine, an antioxidant, such as tocopheryl acetate, and a thickener, such as a carboxyvinyl polymer or hydroxyethyl cellulose.

<Dosage Form>

The norovirus deactivator of the present invention may take any of various dosage forms as required, and for example, may be formed into a liquid formulation, or may be formed into a solid formulation, such as a powder, a tablet, or a capsule.

When the norovirus deactivator is formed into a liquid formulation, its viscosity may be appropriately determined depending on a use method. For example, when the norovirus deactivator is formed into a liquid formulation having a sprayable viscosity, and the liquid formulation is filled into a spray container, e.g., a trigger sprayer, a squeezable container, or an aerosol container, deactivation of norovirus can be easily performed by spraying droplets containing the norovirus deactivator onto a finger, food, cooking equipment, a housing environment, vomit, excrement, or the like. In addition, deactivation of norovirus can also be easily performed by immersing a target of deactivation (e.g., a finger, food, a medical device, a medical instrument, cooking equipment, or a housing environment) in the liquid formulation containing the norovirus deactivator. In addition, the liquid formulation containing the norovirus deactivator may be used in the form of a sheet wetted therewith. Further, the norovirus deactivator may be used as a skin external preparation by being formed into a lotion, a cream, or the like, and thus may be used as an infection prophylactic agent for preventing oral infection with norovirus through deactivation on the spot in case of attachment of norovirus on a finger.

Meanwhile, when the norovirus deactivator is formed into a solid formulation, for example, the norovirus deactivator may be used as an infection prophylactic agent for preventing infection through deactivation of norovirus in case of its entry into the mouth by being orally taken in advance, and even when an infectious disease due to norovirus is developed, the norovirus deactivator may be used as a therapeutic agent for deactivating norovirus in the body. As a method of taking the norovirus deactivator of the present invention, there are given, for example, oral intake, a suppository, a drip, and intravenous injection.

<Method of Deactivating Norovirus>

The present invention encompasses a method of deactivating norovirus through use of a lysozyme component in various environments and situations, such as houses, food factories, public facilities, and hospitals. It should be noted that the case where the deactivation of norovirus is performed as a medical act may be excluded.

Hitherto, lysozyme has been used as a food additive, and salts of the lysozyme have also been used as antimicrobial agents. In particular, lysozyme chloride has been widely used as an antiphlogistic, and its safety has been established. Therefore, a method of using the lysozyme or the salt thereof, or the denatured product thereof is not particularly limited as long as the specificity of the active ingredient of the present invention in deactivating norovirus is not impaired.

That is, depending on the dosage form of the norovirus deactivator described above, there may be adopted a method involving, for example, spraying or applying the norovirus deactivator onto a target region in which norovirus is to be deactivated, mixing the norovirus deactivator with a target in which norovirus is to be deactivated, or allowing the target to take the norovirus deactivator.

<Method of Producing Norovirus Deactivator>

The present invention encompasses a method of producing a norovirus deactivator by incorporating a lysozyme component as an active ingredient for deactivating norovirus into any of various solid or liquid carriers. The present invention particularly encompasses a method of producing a norovirus deactivator by mixing a lysozyme component with a liquid containing at least one kind of a lower alcohol and a polyhydric alcohol, especially a method of producing a norovirus deactivator by mixing a lysozyme component with an alcohol preparation. In this case, a target into which the lysozyme component is incorporated is not particularly limited as long as the specificity of the active ingredient of the present invention in deactivating norovirus is not impaired, and for example, the lysozyme component and the above-mentioned formulation material may be mixed and prepared into a desired dosage form.

<Action and Effect>

The lysozyme component to be used as an active ingredient in the norovirus deactivator of the present invention has an excellent deactivating action on norovirus as compared to each of a persimmon tannin extract (persimmon tannin) and proanthocyanidin contained in grape seeds or the like, which have hitherto been known as active ingredients of norovirus deactivators. In particular, the thermally denatured product can deactivate norovirus within an extremely short action time of 1 minute or less. In addition, hitherto, lysozyme has been used as a food additive for improving the shelf life of food, and lysozyme chloride has been used as an antiphlogistic. Accordingly, the norovirus deactivator of the present invention can be safely used. Further, the persimmon tannin extract (persimmon tannin) and proanthocyanidin contained in grape seeds or the like are both polyphenol-based and dye-based substances, and have a problem of, for example, coloring tableware or equipment when sprayed. However, the norovirus deactivator of the present invention has a white color and does not color tableware or equipment, and hence can be widely used.

EXAMPLES

Now, the present invention is specifically described by way of test examples.

Test Example 1

[1] Preparation of Lysozyme Solution

Norovirus deactivators were each prepared by dissolving egg white (chicken egg white) lysozyme (manufactured by Kewpie Corporation) in distilled water to have a predetermined concentration, and then subjecting the solution to heat treatment under conditions shown in Table 1, followed by air cooling (Test Nos. 2 to 14). In addition, similar egg white lysozyme (unheated lysozyme) was dissolved in water, and the solution was subjected to filter sterilization to prepare a lysozyme solution having a concentration of 10 mass %

(Test No. 1). The result of measurement of the norovirus activity of each solution is shown in Table 1.

The transmittance of the reaction liquid (aqueous solution) in each Test No. for light having a wavelength of 660 nm was measured with an absorptiometer (model name: "UV-2450", manufactured by Shimadzu Corporation).

In each of Test Nos. 8, 9, 11, 13, and 14, changes in transmittance of the reaction liquid described above as the first heating step, the second heating step, and the third heating step were found. In this test example, the first heating step, the second heating step, and the third heating step were successively performed, and the heating time in Table 1 is the total of the heating times in the first, second, and third heating steps.

More specifically, in the heating steps during the preparation of each of the lysozyme denatured products of Test Nos. 8, 9, 11, 13, and 14, it was found that: the transmittance of the reaction liquid for light having a wavelength 660 nm, which was more than 70% (from 99% to 100%) before the first heating step, was decreased to 70% through the first heating step; then, through the second heating step, the transmittance was further decreased and the transmittance of the reaction liquid in the second heating step reached a minimum of less than 70% (from 20% to 30%), followed by an increase in the transmittance again to 70%; and then, through the subsequent third heating step, the transmittance was further increased, and finally, the transmittance of the reaction liquid after the completion of the third heating step was more than 70%.

[2] Evaluation of Infectivity Titer

The infectivity titer of each Test No. was evaluated by a plaque assay method as described below.

(1) In a 6-well plate, murine macrophage established cells (RAW264.7 cells) were cultured to 60% to 80% confluence.

(2) Meanwhile, a virus solution of norovirus having an infectivity titer (PFU/mL) of from about $10^6$ PFU/mL to about $10^7$ PFU/mL was prepared as described below.

First, murine macrophage established cells (RAW264.7 cells) were cultured to confluence, and the confluent cells were inoculated with 1 mL of a norovirus solution, followed by culture for 2 days under the conditions of 37° C. and 5% $CO_2$. In this case, Murine norovirus strain 1 (MNV-1) (Effect of Food Residues on Norovirus Survival on Stainless Steel Surfaces) was used as the norovirus solution.

After the culture, detachment of the cells was confirmed by visual observation, and the cells were disrupted by repeating freezing and thawing four times to release the virus in the cells. After that, the resultant was dispensed into a 50 mL centrifuge tube and centrifuged (8,000 g, 20 minutes) to afford a norovirus solution having an infectivity titer (PFU/mL) of from about $10^6$ PFU/mL to about $10^7$ PFU/mL. The norovirus solution was preserved at −80° C. and thawed before use.

(3) Equal amounts of the norovirus solution obtained in (2) were added to the lysozyme solutions of Test Nos. 1 to 14, and the mixtures were used as samples for evaluation of Test Nos. 1 to 14.

TABLE 1

| Test No. | Kind of lysozyme component | Heating temperature × heating time | Lysozyme concentration in aqueous solution [mass %] | 0 minutes from start of contact | 1 minute from start of contact | 60 minutes from start of contact | Fluorescence intensity |
|---|---|---|---|---|---|---|---|
| | | Preparation conditions | | Infectivity titer of norovirus | | | |
| 1 | Unheated lysozyme | — | 10 | Comparable effect to that of Test No. 2 | — | — | 280 or less |
| 2 | Lysozyme denatured product | 60° C. × 10 min | 2 | $3.3 \times 10^7$ | — | $1.9 \times 10^2$ | 280 or less |
| 3 | Lysozyme denatured product | 80° C. × 10 min | 2 | $1.9 \times 10^6$ | $2.7 \times 10^5$ | — | 280 or less |
| 4 | Lysozyme denatured product | 80° C. × 30 min | 2 | $1.9 \times 10^6$ | $1.0 \times 10^4$ | — | 280 |
| 5 | Lysozyme denatured product | 80° C. × 30 min | 0.2 | Slightly stronger effect than that of Test No. 2 | — | — | 280 or less |
| 6 | Lysozyme denatured product | 80° C. × 30 min | 0.1 | Comparable effect to that of Test No. 2 | — | — | 280 or less |
| 7 | Lysozyme denatured product | 80° C. × 60 min | 2 | $4.6 \times 10^6$ | $3.7 \times 10^3$ | — | 3,600 |
| 8 | Lysozyme denatured product | 80° C. × 90 min | 2 | $4.6 \times 10^6$ | $1.6 \times 10^3$ | — | 5,400 |
| 9 | Lysozyme denatured product | 80° C. × 180 min | 2 | $4.6 \times 10^6$ | $1.1 \times 10^2$ | — | 5,700 |
| 10 | Lysozyme denatured product | 90° C. × 30 min | 2 | $4.6 \times 10^6$ | $2.1 \times 10^3$ | — | 2,000 |
| 11 | Lysozyme denatured product | 90° C. × 60 min | 2 | $4.6 \times 10^6$ | 10 or less | — | 5,600 |
| 12 | Lysozyme denatured product | 100° C. × 10 min | 2 | $4.6 \times 10^6$ | $9.8 \times 10^4$ | — | Less than 4,000 |
| 13 | Lysozyme denatured product | 100° C. × 40 min | 2 | $4.6 \times 10^6$ | 10 or less | — | 6,400 |
| 14 | Lysozyme denatured product | 121° C. × 15 min | 2 | $4.6 \times 10^6$ | $6.5 \times 10^3$ | — | 4,000 or more |

Each sample for evaluation was left to stand at room temperature for a predetermined reaction time (0 minutes, 1 minute, or 60 minutes) to allow the lysozyme and the norovirus in each sample for evaluation to react with each other.

After the reaction, each sample for evaluation was diluted by a factor of $10^x$ to afford a diluted sample. Here, x represents an integer, and is set to such a number that the number of plaques may be counted by visual observation in (8) below. That is, the dilution factor was adjusted so that the number of plaques was from about 10 to about 100 in (8).

(4) The whole amount of the culture solution in the plate of (1) was discarded, and each diluted sample obtained by the dilution after the standing for the predetermined period of time was inoculated into two wells at 500 μL/well.

(5) While shaking was performed so as to prevent the murine macrophage established cells (RAW264.7 cells) from being dried, incubation was performed at room temperature for 1 hour to infect the murine macrophage established cells with norovirus.

(6) The whole amount of 500 μL/well of the inoculation solution on the plate was removed, and 1.5% Sea Plaque Agarose-DMEM (37° C.) was overlaid at 2 ml/well. After its solidification, culture was performed under the conditions of 37° C. and 5% $CO_2$ for 2 days.

(7) The plate after the culture for 2 days was overlaid with a 0.03% neutral red solution serving as a stain at 2 mL/well, followed by incubation under the conditions of 37° C. and 5% $CO_2$ for 1 hour.

(8) After the incubation of (7), the whole amount of the 0.03% neutral red solution was discarded, and the number of plaques was counted by visual observation. An infectivity titer (PFU/mL) was calculated from the resultant number of plaques and the dilution factor.

(9) In addition, on the basis of the results shown in Table 1, the anti-norovirus activity of each of Test Nos. 3 to 14 was calculated from the following equation. It was found from the results that in each of the cases of Test Nos. 8, 9, 11, 13, and having a fluorescence intensity of 4,000 or more, the anti-norovirus activity specified by the following equation was 2 or more.

Anti-norovirus activity=$Log_{10}$(infectivity titer of norovirus mixed liquid before standing for 1 minute)−$Log_{10}$(infectivity titer of norovirus mixed liquid after standing for 1 minute)

It was found from the results that each of the lysozyme denatured products of Test Nos. 8, 9, 11, 13, and 14 was able to decrease the infectivity titer of norovirus to $\frac{1}{10^2}$th or less through contact with norovirus, and thus had a norovirus deactivating effect.

In addition, the lysozyme denatured product (Test No. 6) and the unheated lysozyme (Test No. 1) each exhibited a comparable deactivating effect on norovirus to that of the lysozyme denatured product of Test No. 2, and the lysozyme denatured product (Test No. 5) exhibited a slightly stronger deactivating effect on norovirus than that of the lysozyme denatured product of Test No. 2.

Test Example 2

Lysozyme denatured products having fluorescence intensities shown in Table 2 were obtained by changing, in Test Example 1, the heating time and heating temperature of lysozyme and the concentration of the lysozyme aqueous solution.

TABLE 2

| | | Preparation conditions | | |
|---|---|---|---|---|
| Test No. | Kind of lysozyme component | Heating temperature × heating time | Lysozyme concentration in aqueous solution [mass %] | Fluorescence intensity |
| 15 | Lysozyme denatured product | 80° C. × 180 min | 5 | 5,500 |
| 16 | Lysozyme denatured product | 87° C. × 180 min | 4 | 7,500 |
| 17 | Lysozyme denatured product | 90° C. × 60 min | 5 | 6,400 |
| 18 | Lysozyme denatured product | 95° C. × 180 min | 2 | 5,000 |
| 19 | Lysozyme denatured product | 95° C. × 180 min | 7 | 6,000 |

Test Example 3

In this test example, electrophoresis was performed for a lysozyme denatured product. In this test example, a lysozyme denatured product was prepared by changing the heating conditions (heating temperature, heating time, and concentration of egg white lysozyme) in Test Example 1.

More specifically, a 2 mass % aqueous solution of egg white lysozyme was collected at a heating temperature of 80° C. at heating time points of 0 minutes, 15 minutes, 30 minutes, 60 minutes, 90 minutes, and 120 minutes, and 950 μL of a sample buffer was added to 50 μL of the aqueous solution. The mixture was heated at 100° C. for 10 minutes and then cooled with ice, and 10 μL of the resultant (10 μg in terms of the lysozyme denatured product) was charged to an electrophoresis gel. The sample buffer used had added thereto no 2-mercaptoethanol (non-reduced). The electrophoresis gel used was SDS-PAGEmini (manufactured by TEFCO, gel concentration: from 4% to 10%, gel thickness: 1 mm), and electrophoresis was performed at a constant current of 20 mA. Coomassie Blue R250 was used as a stain.

Figure 2:
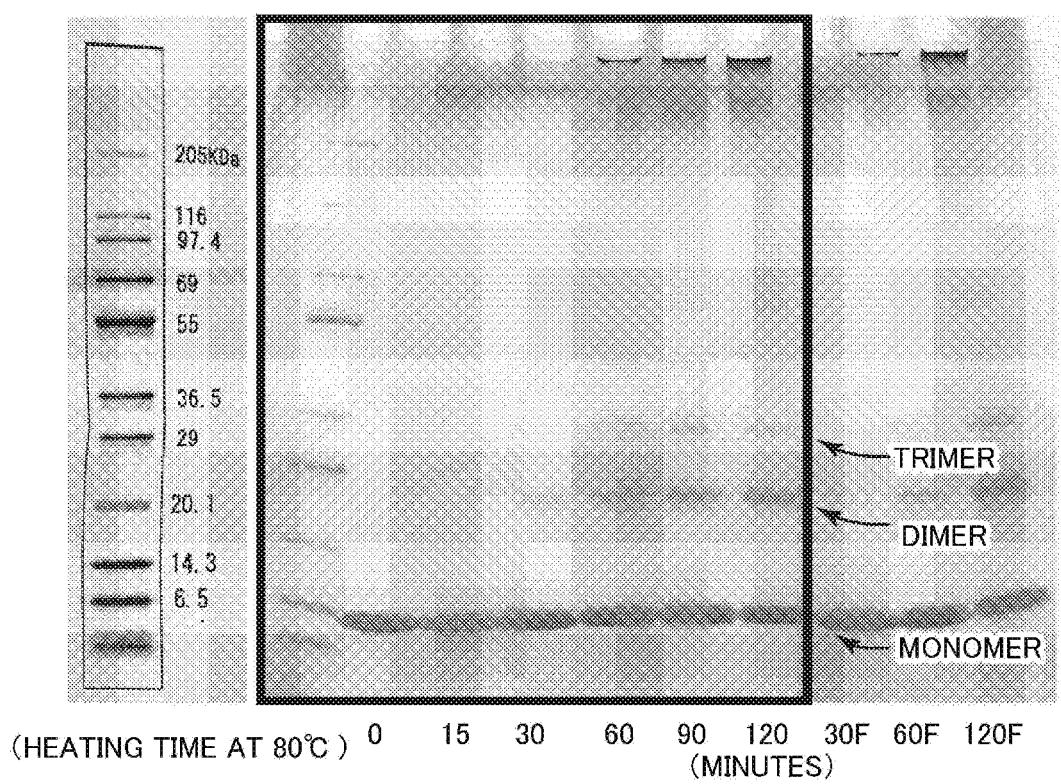
FIG. 2 is a photograph for showing the results of electrophoresis (SDS-PAGE) of lysozyme components (denatured products of lysozyme and/or a salt thereof) obtained in one Example of the present invention.

FIG. 2 is a photograph for showing the results of the electrophoresis. As shown in FIG. 2, at the heating time points of 60 minutes, 90 minutes, and 120 minutes, bands indicating an about 29 KDa protein (presumed to be a dimer) and/or an about 36.5 KDa protein (presumed to be a trimer) were clearly detected. In addition, it was found that as the heating time became longer, the bands indicating those proteins became more intense (the amounts of the proteins generated increased). In addition, at the same heating temperature, it is presumed that as the heating time becomes longer, the surface hydrophobicities of the proteins increase to provide proteins having higher norovirus deactivating actions.

Test Example 4

In this test example, contact between norovirus and a lysozyme component was photographed using an electron microscope.

Norovirus: The norovirus used was MNV-1 (provided by Dr. Herbert W. Virgin at Washington University). In addition, a norovirus solution having removed therefrom a medium component was prepared. A method for the preparation of the norovirus solution is as described below.

Test sample: Lysozyme denatured products obtained by heating each 2 mass % aqueous solution of egg white lysozyme at 80° C. for 180 minutes (Test No. 9) were used. A thermostatic water bath was used for the heating.

A period of time of contact between the norovirus and the lysozyme denatured product was set to each of 1 minute and 1 hour.

Test Method (Native Staining Method):

1) The test sample was dropped onto Parafilm to be brought into contact on a carbon support film for 2 minutes.

2) The test sample obtained in 1) was brought into contact on 2 mass % uranium acetate for 2 minutes.

3) An unnecessary liquid on the test sample obtained in 2) was absorbed with filter paper, and the test sample was dried.

4) An electron microscope photograph was taken with an electron microscope (JEOL JEM1200EX) at 80 kV.

Figure 3A:
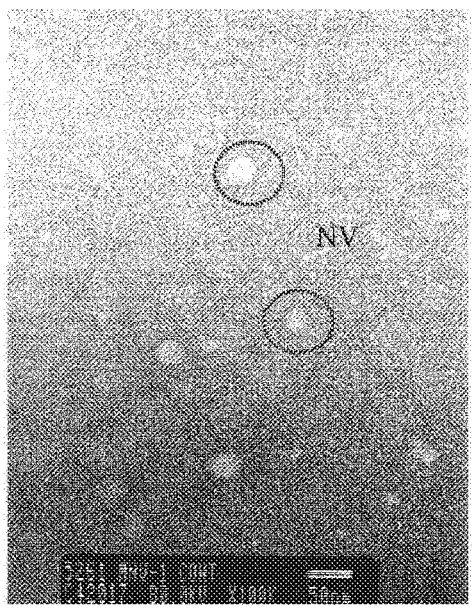
FIG. 3A is an electron micrograph of norovirus.
Figure 4A:
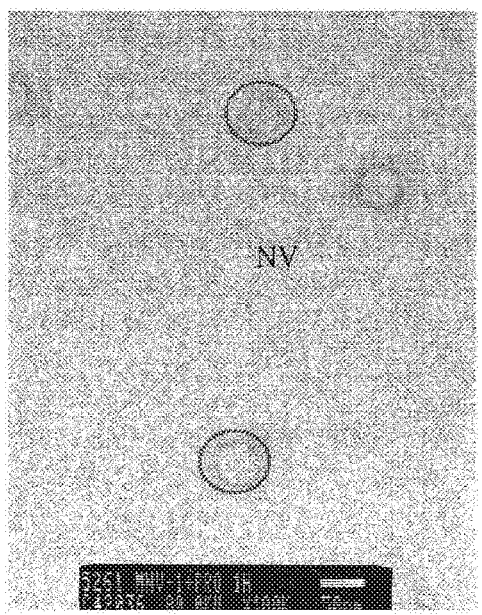
FIG. 4A is an electron micrograph of norovirus and a lysozyme component (lysozyme denatured product obtained by heating of 80° C.×180 minutes) at a time point of 1 hour from the start of contact.
Figure 4B:
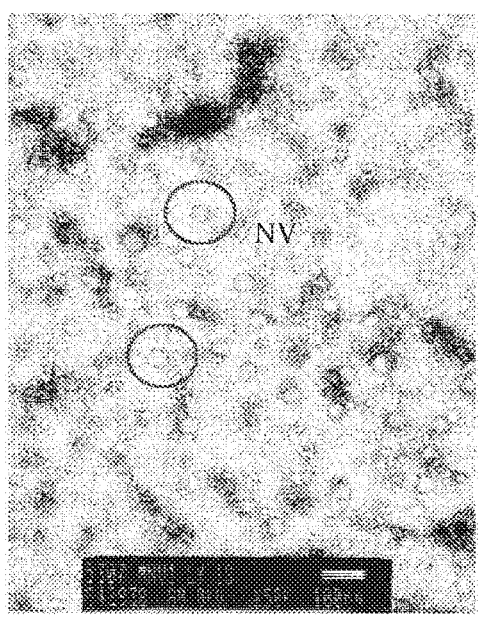
FIG. 4B is an electron micrograph of norovirus and a lysozyme component (unheated lysozyme) at a time point of 1 minute from the start of contact.

Discussion:

In the literature, the size (diameter) of norovirus is said to be from 30 nm to 40 nm. In FIG. 3A, FIG. 4A, and FIG. 4B, "NV" represents norovirus, and encircled portions correspond to norovirus.

As shown in FIG. 3A, in this test example, a spherical object having a diameter of from 30 nm to 40 nm, which was nearly the same size as the size of norovirus described in the literature, was able to be observed. Judging from the size, it is presumed that the spherical object is norovirus.

Figure 3B:
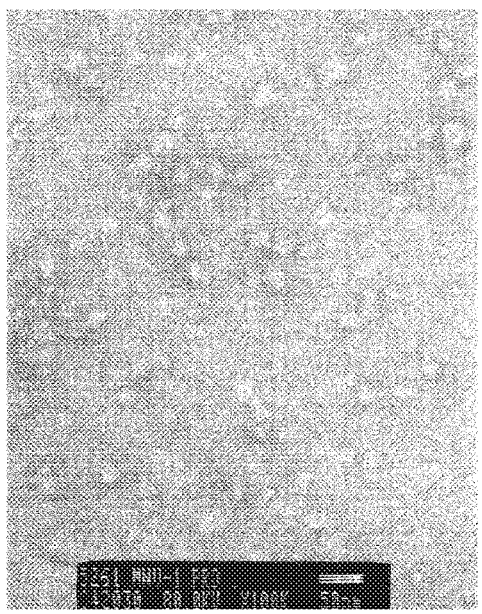
FIG. 3B is an electron micrograph of a lysozyme component (lysozyme denatured product obtained by heating at 80° C. for 180 minutes).

In addition, as shown in FIG. 3B, non-spherical and irregular objects were able to be observed. Lysozyme (unheated) is known to be a particle having a size (diameter) of from 3 nm to 4 nm. From this fact, it is presumed that those objects are lysozyme that has been denatured by heating to be changed in shape.

Figure 3C:
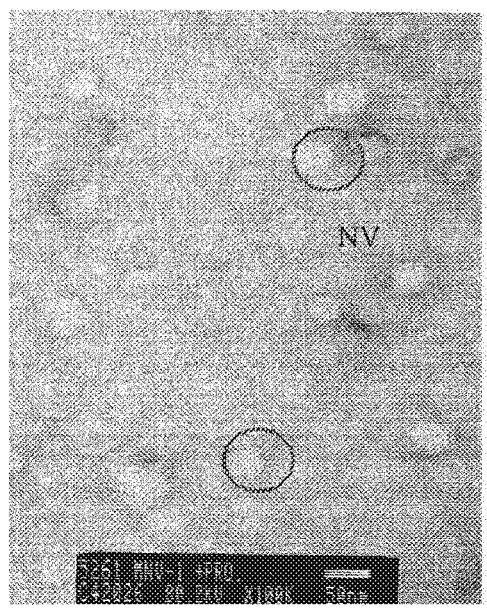
FIG. 3C is an electron micrograph of norovirus and the lysozyme component (lysozyme denatured product) at a time point of 1 minute from the start of contact.

As shown in FIG. 3C, at the time point of 1 minute from the start of contact with norovirus, a spherical body that was presumably swollen norovirus was observed.

In addition, as shown in FIG. 4A, also at the time point of 1 hour from the start of contact with norovirus, the spherical body that was presumably swollen norovirus, which was observed at the time point of 1 minute from the start of contact with norovirus ((FIG. 3C), was observed. In addition, at this time point, as compared to the time point of 1 minute from the start of contact with norovirus, general reductions in norovirus counts were observed. This agrees with the reduction in viable norovirus count to ¹/₁,₀₀₀th or less due to the lysozyme denatured product obtained by heating at 80° C. for 180 minutes described above. Meanwhile, as shown in FIG. 4B, at the time point of 1 minute from the start of contact between norovirus and lysozyme (unheated), no change in norovirus was observed.

In addition, the diameter of norovirus in the case of contact with a solution of lysozyme (or the lysozyme denatured product) was as described below.

Norovirus: 35.5±1.70 nm
Unheated lysozyme: 37.3±1.77 nm
Lysozyme denatured product (heating of 80° C.×180 minutes: 49.1±2.12 nm)

It was found from this test example that norovirus was swollen through contact with the lysozyme denatured product. Thus, it is presumed that norovirus is deactivated as a result of the swelling of norovirus through contact with the lysozyme denatured product.

Test Example 5

In this test example, the effect of a lysozyme denatured product on human norovirus was investigated using a real-time PCR method. A human norovirus solution used in this test was prepared as follows: a human norovirus undiluted solution, which had been collected from an excretion of a patient and cryopreserved at −80° C., was thawed on ice and diluted with phosphorus-buffered physiological saline by a factor of 10, followed by centrifugation at 10,000 rpm for 20 minutes and removal of a precipitate.

Test Method (Real-Time PCR Method):

The human norovirus solution was mixed with an equal amount of the lysozyme solution of Test No. 13 or distilled water, and the mixture was left standing for 1 hour. Then, a human norovirus gene amount was measured by a real-time PCR method involving using a Takara qPCR Norovirus (GI/GII) Typing kit.

Figure 5:
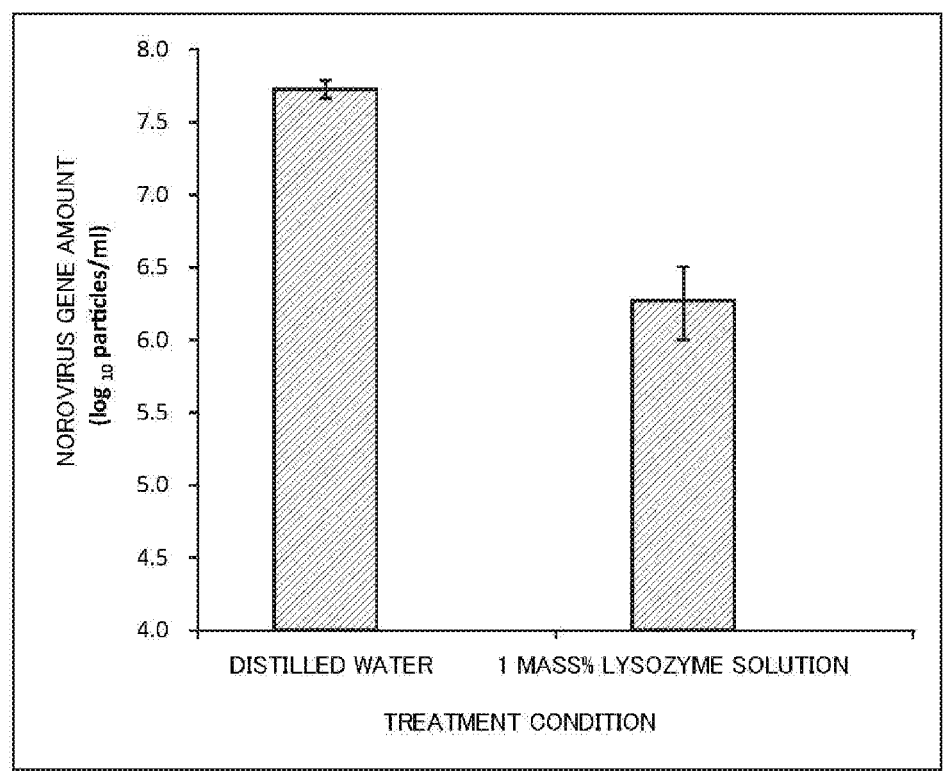
FIG. 5 is the result of analysis of a human norovirus gene amount by a real-time PCR method after contact between human norovirus and a lysozyme component of the present invention (100° C.×40 minutes) for 1 hour.

As a result, it was found that the human norovirus gene amount remaining in the mixed liquid with the lysozyme solution of Test No. 13 (right side of FIG. 5) was smaller than the human norovirus gene amount remaining in the mixed liquid with distilled water (left side of FIG. 5) by 1.5 $\log_{10}$ particles/mL. This suggested that the lysozyme denatured product killed human norovirus (FIG. 5).

Formulation Example 1

A soft capsule containing the following formulation was prepared using the lysozyme denatured product (Test No. 9) of Test Example 1.

| <Proportion of Formulation> | |
|---|---|
| Lysozyme denatured product (Test No. 9) | 20% |
| Olive oil | 50% |
| Beeswax | 10% |
| Medium chain fatty acid triglyceride | 10% |
| Emulsifier | 10% |
| Total | 100% |

Formulation Example 2

A powder (granule) containing the following formulation was prepared using the lysozyme denatured product (Test No. 11) of Test Example 1.

| <Proportion of Formulation> | |
|---|---|
| Lysozyme denatured product (Test No. 11) | 10% |
| Lactose | 60% |
| Corn starch | 25% |
| Hypromellose | 5% |
| Total | 100% |

Formulation Example 3

A tablet containing the following formulation was prepared using the lysozyme denatured product (Test No. 13) of Test Example 1.

| <Proportion of Formulation> | |
|---|---|
| Lysozyme denatured product (Test No. 13) | 25% |
| Lactose | 24% |
| Crystalline cellulose | 20% |
| Corn starch | 15% |

-continued

| <Proportion of Formulation> | |
| --- | --- |
| Dextrin | 10% |
| Emulsifier | 5% |
| Silicon dioxide | 1% |
| Total | 100% |

INDUSTRIAL APPLICABILITY

The present invention is effective in various situations of deactivating norovirus, and is useful as, for example, a disinfectant for disinfecting fingers, the body, medical instruments, facilities including schools, hospitals, and welfare facilities, factories, houses, and the like, a food additive, an agent for removing norovirus, or an infection prophylactic or therapeutic agent.

Embodiments according to the present invention have been described above. The present invention encompasses substantially the same configurations as the configurations described in the embodiments (e.g., configurations having the same functions, methods, and results, or configurations having the same objects and results). In addition, the present invention encompasses configurations obtained by replacing non-essential parts of the configurations described in the embodiments. In addition, the present invention encompasses configurations exhibiting the same action and effect or configurations capable of achieving the same objects as those of the configurations described in the embodiments. In addition, the present invention encompasses configurations obtained by adding known technologies to the configurations described in the embodiments.

The invention claimed is:

1. A method of deactivating norovirus, the method comprising deactivating norovirus using a norovirus deactivator,
    wherein the norovirus deactivator comprises a lysozyme component that comprises at least one kind selected from the group consisting of a denatured product of a lysozyme and a denatured product of a salt of a lysozyme,
    wherein a total content of the lysozyme component in the norovirus deactivator is 0.05 mass % or more,
    wherein the lysozyme component has a fluorescence intensity of 4,000 or more,
    wherein the fluorescence intensity is a value measurable using a fluorescence spectrophotometer of model FP-8500 from JASCO Corporation, under conditions of an excitation wavelength of 390 nm with an excitation band width of 10 nm, a fluorescence wavelength of 470 nm with a fluorescence band width of 10 nm for a liquid obtained by adding 25 µL of a methanol solution of 8 mM 1,8-anilinonaphthalenesulfonic acid to 5 mL of a dilution obtained by diluting the lysozyme component with a phosphate buffer having a pH of 7.0 so as to have a concentration of the lysozyme component of 0.05 mass % in terms of solid content, and to have a concentration of phosphate of 0.2 M and then subjecting the liquid to a reaction at room temperature for 30 minutes.

2. The method of deactivating norovirus according to claim 1, wherein the lysozyme component has an anti-norovirus activity of 2.0 or more,
    wherein the anti-norovirus activity is a value obtained by subtracting, when a norovirus-containing liquid obtained by mixing equal amounts of a norovirus solution and a 2 mass % aqueous solution of the lysozyme component is left standing at room temperature for 1 minute, a logarithm of an infectivity titer after the standing from a logarithm of an infectivity titer before the standing.

3. The method of deactivating norovirus according to claim 1, wherein the deactivation of the norovirus comprises spraying or applying the norovirus deactivator onto a target region in which norovirus is to be deactivated, or mixing the norovirus deactivator with a target in which norovirus is to be deactivated.

4. The method of deactivating norovirus according to claim 1, wherein the norovirus deactivator is formed into a liquid formulation.

5. The method of deactivating norovirus according to claim 4, wherein the liquid formulation is filled into a spray container and has a viscosity sufficient to be sprayed from the spray container.

* * * * *